(12) United States Patent
Harrold et al.

(10) Patent No.: US 6,565,586 B2
(45) Date of Patent: May 20, 2003

(54) KERATOME BLADE HOLDER

(75) Inventors: Lewis Harrold, Winter Springs, FL (US); Miguel Cabada, Winter Springs, FL (US)

(73) Assignee: LaserSight Technologies, Inc., Winter Park, FL (US)

( * ) Notice: Subject to any disclaimer, the term of this patent is extended or adjusted under 35 U.S.C. 154(b) by 0 days.

(21) Appl. No.: 09/907,740

(22) Filed: Jul. 19, 2001

(65) Prior Publication Data

US 2002/0065532 A1 May 30, 2002

Related U.S. Application Data

(60) Provisional application No. 60/253,720, filed on Nov. 29, 2000.

(51) Int. Cl.⁷ .................................................. A61F 9/00
(52) U.S. Cl. .................................................. 606/166
(58) Field of Search ............................. 606/166, 167, 606/170, 79, 84, 82, 90, 88, 87; 30/346.53, 346.54, 350, 74

(56) References Cited

U.S. PATENT DOCUMENTS

| | | | |
|---|---|---|---|
| 1,495,921 A | * | 5/1924 | Moulton |
| 3,031,757 A | * | 5/1962 | Kramer |
| 3,660,894 A | * | 5/1972 | Sand |
| 4,517,741 A | * | 5/1985 | Castelluzzo ............... 221/212 |
| 4,700,600 A | * | 10/1987 | Pickett ....................... 83/165 |
| 5,817,097 A | * | 10/1998 | Howard et al. ............ 606/82 |
| 6,233,830 B1 | * | 5/2001 | Lamond et al. ............ 30/123 |
| 2002/0107521 A1 | * | 8/2002 | Petersen et al. ........... 606/85 |

* cited by examiner

*Primary Examiner*—David O. Reip
*Assistant Examiner*—D. Jacob Davis
(74) *Attorney, Agent, or Firm*—William H. Bollman

(57) ABSTRACT

A blade holder is provided for receiving and holding a keratome blade. The keratome blade used with the blade holder is of material so as to be attracted to a magnetic field. The blade holder includes a handle portion configured to be grasped by a user. A head portion is coupled to the handle portion and has a receiving surface sized to receive at least a portion of the keratome blade. The head portion is constructed and arranged to facilitate application of a magnetic field to attract the keratome blade such that the keratome blade can be carried by the receiving surface of the head portion. Hence, the blade can be inspected and loaded into a keratome having only been contacted by the sterile blade holder.

10 Claims, 4 Drawing Sheets

KERATOME BLADE HOLDER

This application is based on U.S. Provisional Application No. 60/253,720, filed on Nov. 29, 2000, and claims the benefit thereof for priority purposes. This U.S. Provisional Application is expressly incorporated herein by reference.

FIELD OF THE INVENTION

The invention generally relates to blade holders and, more particularly, to a keratome blade holder for handling a keratome blade without damaging the blade or introducing particulates on the blade prior to being loaded into a keratome.

BACKGROUND OF THE INVENTION

Keratome blades for cutting eye tissue are typically contained in sterile packaging. When a blade is to be inserted into a keratome, the package is opened and the blade is grasped by a user typically with gloved covered fingers. Oftentimes the blade is inspected under a microscope to ensure that the cutting edge of the blade is intact. Inspection may be difficult with tweezers or finger grasping since in either case, the user must exert a force on the blade to hold the blade. After inspection, the blade is manually placed onto a blade support that is inserted into a keratome. During this process there is a possibility that contaminants or particulates can be introduced to the blade or the cutting edge may be damage. Furthermore, in handling the blade with fingers, the user faces a risk of being cut by the blade.

There is a need to provide a hand-held blade holder for receiving and holding a keratome blade such the blade may be manipulated easily and in a sterile manner.

SUMMARY OF THE INVENTION

An object of the invention is to fulfill the need referred to above. In accordance with the principles of the present invention, this objective is achieved by providing a blade holder for receiving and holding a keratome blade. The keratome blade is of material so as to be attracted to a magnetic field. The blade holder includes a handle portion configured to be grasped by a user. A head portion is coupled to the handle portion and has a receiving surface sized to receive at least a portion of the keratome blade. The head portion is constructed and arranged to facilitate application of a magnetic field to attract the keratome blade such that the keratome blade can be carried by receiving surface of the head portion. Hence, the blade can be inspected and loaded into a keratome having only been contacted by the sterile blade holder.

Other objects, features and characteristics of the present invention, as well as the methods of operation and the functions of the related elements of the structure, the combination of parts and economics of manufacture will become more apparent upon consideration of the following detailed description and appended claims with reference to the accompanying drawings, all of which form a part of this specification.

BRIEF DESCRIPTION OF THE DRAWINGS

The invention will be better understood from the following detailed description of the preferred embodiments thereof, taken in conjunction with the accompanying drawings, wherein like reference numerals refer to like parts, in which.

DETAILED DESCRIPTION OF THE PREFERRED EMBODIMENT

Figure 1:
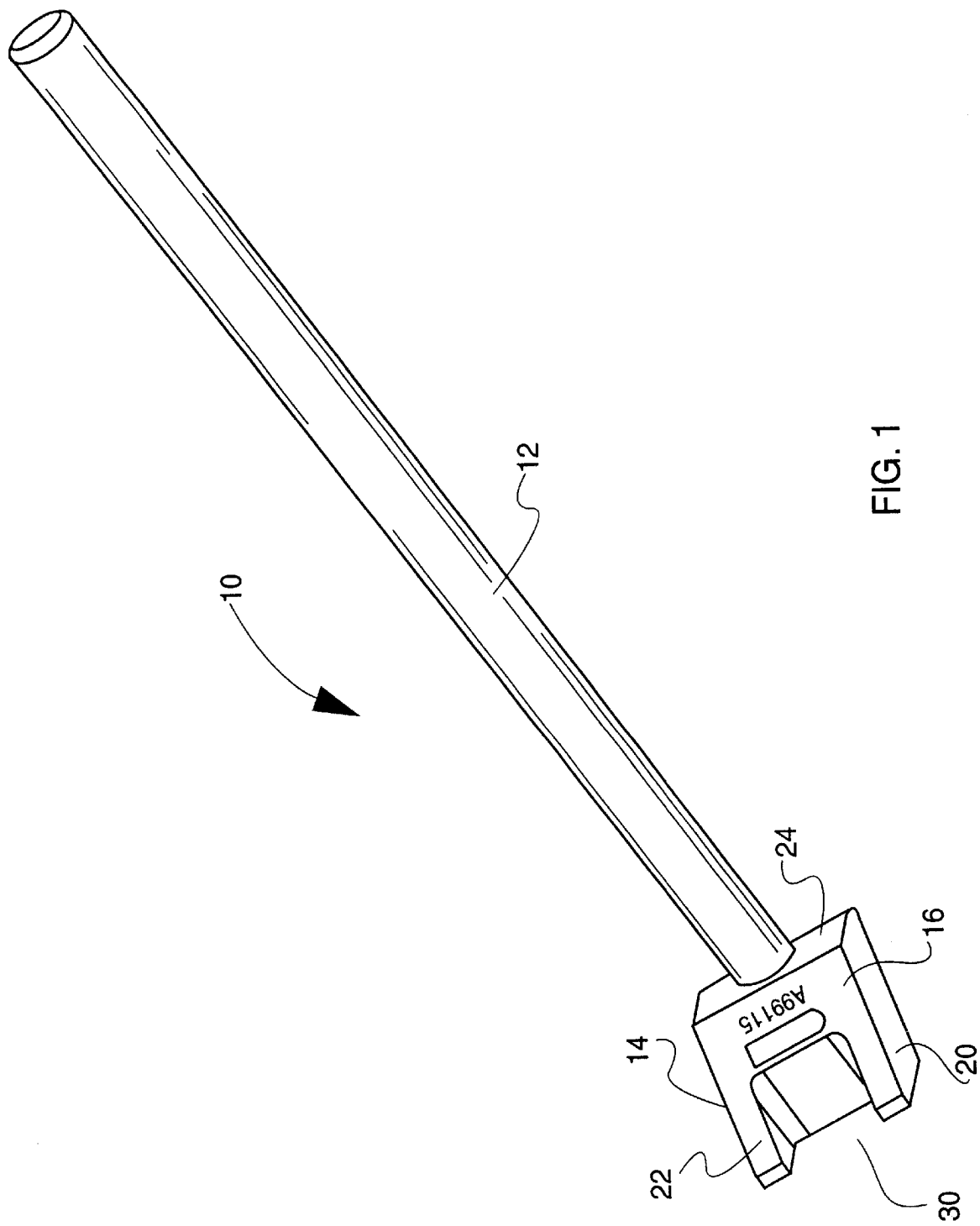
FIG. 1 is a top perspective view of a blade holder provided in accordance with the principles of the present invention.

With reference to FIG. 1, blade holder, provided in accordance with the principles of the invention, is shown generally indicated at 10. The blade holder 10 includes a handle portion 12 and a head portion 14 coupled to an end of the handle portion 12. The handle portion 12 is sized to be grasped easily by a user's fingers. In the illustrated embodiment, the handle portion 12 is preferably cylindrical for ease of manufacture. The handle portion 12 may have any elongated configuration, such as, for example, square, rectangular, triangular, octangonal, ribbed, and/or oval cross-section. The handle portion 12 and head portion 14 are preferably made of metal so as withstand repeated sterilizations. However, the handle portion 12 may be comprised of other materials such as plastic.

Figure 3:
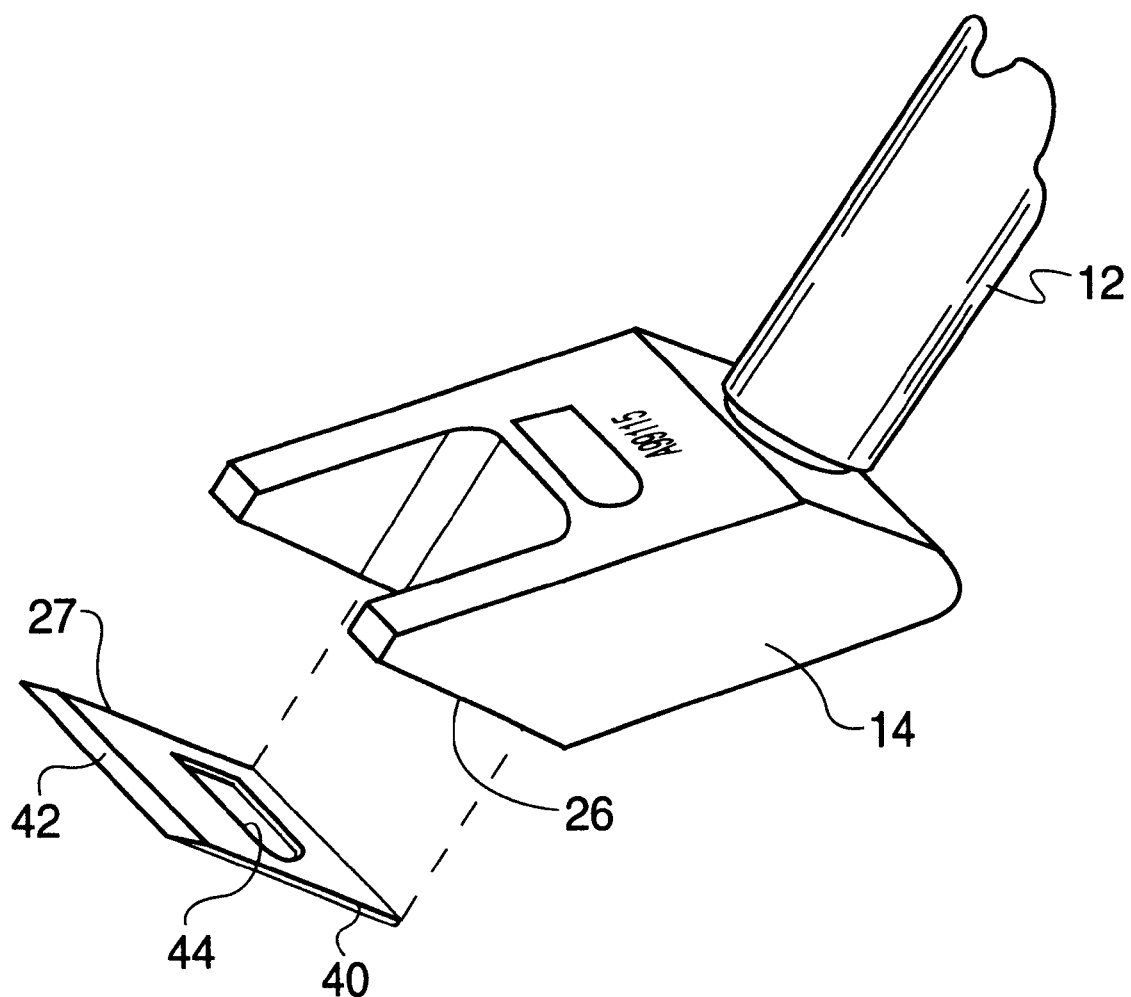
FIG. 3 is a perspective view of the blade holder of the invention shown attracting a keratome blade.
Figure 4:
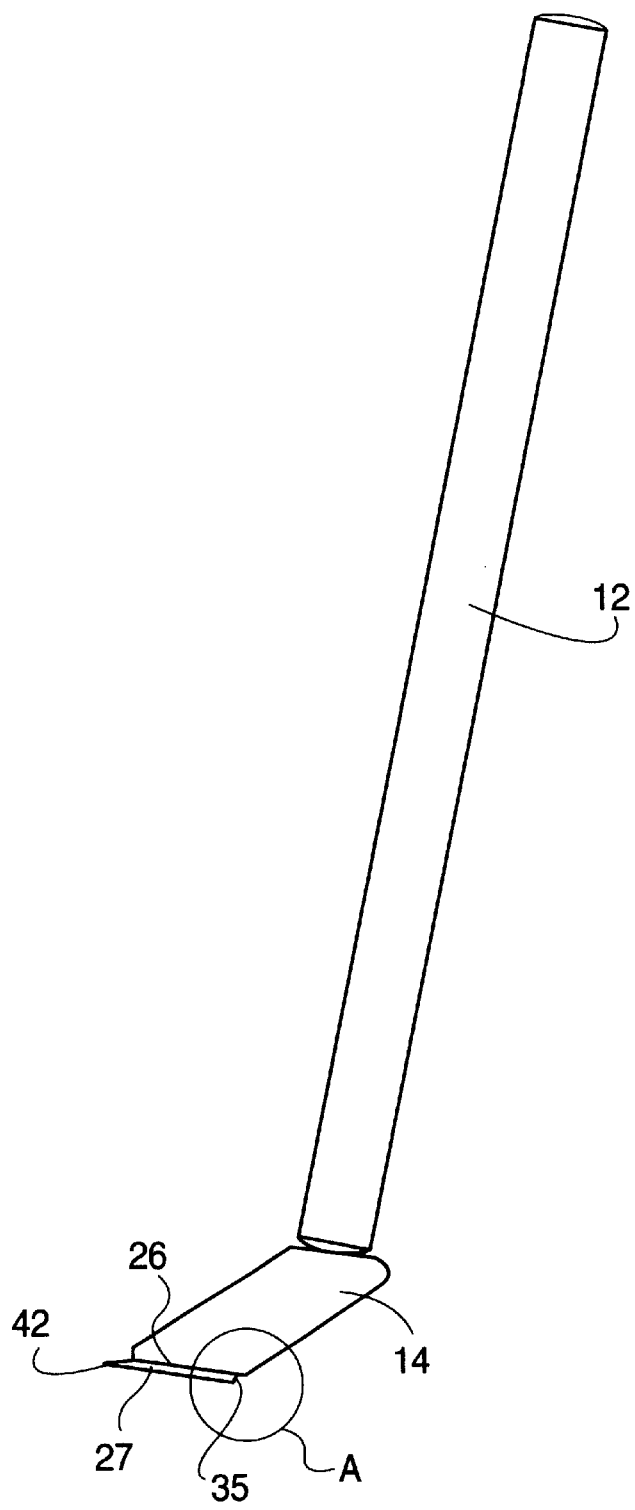
FIG. 4 is side view of the blade holder of the invention with a keratome blade being carried by the head portion thereof.
Figure 5:
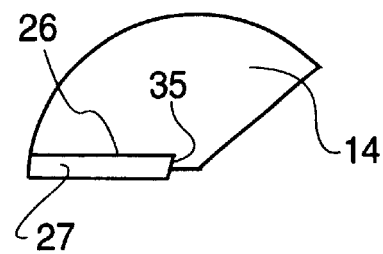
FIG. 5 is an enlarged view the portion A encircled in FIG. 4.

In the illustrated embodiment, the head portion 14 has a top surface 16, a bottom surface 18, a pair of sides 20 and 22, a back surface 24 and a front surface 26. The back surface 24 is coupled to the handle portion 12. The front surface 26 is generally planar and of generally U-shape defined by a base 28 and first and second arms 30 and 32, respectively, each extending from the base 28 and disposed in spaced relation to define a channel 34 therebetween, the function of which will be explained below. A portion 35 (FIG. 5) protrudes from the base 28 to define a step, which functions as a seat for a keratome blade when a blade is received by the head portion 14. The front or receiving surface 26 of the head portion 14 is sized to receive a keratome blade 27 such that the cutting edge 42 of the blade 27 extends beyond surface 26 so as to be inspected (FIG. 4). A conventional keratome blade 27 is shown in FIG. 3 such as the UltraEdge™ keratome blade commercially available from LaserSight Technologies, Inc. in Winter Park, Fla. The keratome blade 27 is of a material that is attracted to a magnetic field, such as any material containing iron. The front surface 26 can be curved to accommodate curved blades.

Figure 2:
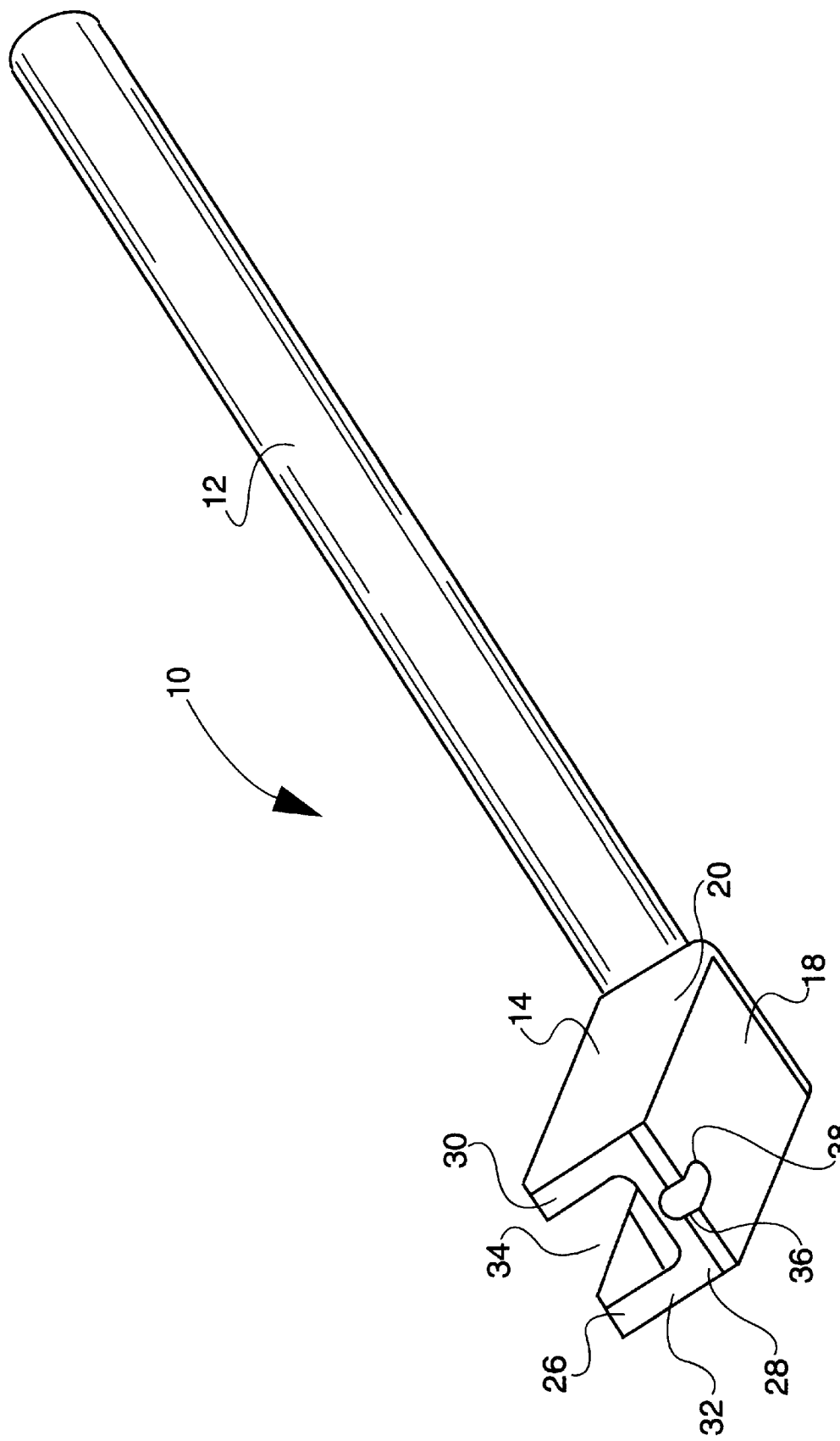
FIG. 2 is a bottom perspective view of the blade holder of the invention.

As shown in FIG. 2, a magnet 36 (preferably an Alnico magnet) is in the form of a pellet and is coupled to the head portion 14 near base 28. More particularly, the head portion 14 includes a recess 38 and the magnet 36 is received in the recess 38 so as to be flush with the front surface 26. The depth of the recess 38 and the strength of the magnet 36 are such that when the head portion 14 is moved towards a keratome blade 27, as in FIG. 3, the magnetic field of the magnet 36 is just strong enough to pick-up and retain the blade 27 at the front surface 26 without being so forceful that the blade 27 "leaps" up to the head portion 14, which may cause damage to the blade 27. Alternatively, the entire head portion may be magnetized so long as the magnetic force does not cause the blade 27 to "leap" to the head portion 14. The magnet 36 can be of any material. Instead of using a magnet, the magnetic field can be generated by an electromagnet.

With reference to FIGS. 3 and 4, when a blade 27 is to be carried by the blade holder 10, the head portion of the blade holder 10 is moved towards the blade 27. The magnetic field causes the planar surface 40 of the blade 27 to rest on front surface 26 with the cutting edge 42 of the blade 27 extending from the front surface 26 and a rear edge of the blade being seated at the step 35. This positioning of the blade 27 with respect to the head portion 14 permits the cutting edge 42 to be inspected under a microscope for defects. Due to the channel 34 of the head portion 14, a cutout 44 of the blade 27 (FIG. 3) is accessible such that the blade 27 can be placed on a blade support (not shown), with the cutout 44 being received by a protrusion of the blade support. The blade support can then be inserted into a keratome. Hence, the blade 27 can be inspected and loaded into a keratome having only been contacted by the sterile blade holder 10.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. A blade holder for receiving and holding a keratome blade, the keratome blade being of material so as to be attracted to a magnetic field, the blade holder comprising:
   a handle portion configured to be grasped by a user; and
   a head portion coupled to the handle portion, the head portion having a receiving surface sized to receive at least a portion of the keratome blade, the head portion being constructed and arranged to facilitate application of a magnetic field to attract the keratome blade such that the keratome blade can be carried by the receiving surface of the head portion;
   wherein the receiving surface is defined by a base and first and second arms extending from the base, the first and second arms being disposed in spaced relation to define a channel therebetween.

2. The blade holder of claim 1, wherein the base includes a portion protruding therefrom to define a step.

3. A blade holder for receiving and holding a keratome blade, the keratome blade being of material so as to be attracted to a magnetic field, the blade holder comprising:
   a handle portion configured to be grasped by a user; and
   a head portion coupled to the handle portion and including means for facilitating application of a magnetic field so as to attract the keratome blade such that the keratome blade can be carried by a receiving surface of the head portion;
   wherein the receiving surface is defined by a base and first and second arms extending from the base, the first and second arms being disposed in spaced relation to define a channel therebetween.

4. The blade holder of claim 3, wherein the base includes a portion protruding therefrom to define a step.

5. A blade holder for receiving and holding a keratome blade, the keratome blade being of material so as to be attracted to a magnetic field, the blade holder comprising:
   an elongated handle portion configured to be grasped by a user,
   a head portion coupled to the handle portion, the head portion having a generally U-shaped receiving surface defined by a base and first and second arms extending from the base, the first and second arms being disposed in spaced relation to define a channel therebetween, the receiving surface being sized to receive at least a portion of the keratome blade, and
   a magnet coupled to the head portion so as to provide a magnetic field near the receiving surface to attract the keratome blade such that the keratome blade can be carried by the receiving surface.

6. The blade holder of claim 5, wherein the receiving surface is a generally planar surface.

7. The blade holder of claim 5, wherein the magnet is disposed in a recess in the head portion and is flush with the receiving surface.

8. The blade holder of claim 5, wherein the base includes a portion protruding therefrom to define a step.

9. The blade holder of claim 5, wherein the handle portion and the head portion are each composed of metal.

10. The blade holder of claim 5, in combination with a keratome blade composed of a material that is attracted to the magnetic field.

* * * * *